(12) United States Patent
Sberveglieri et al.

(10) Patent No.: US 7,441,440 B2
(45) Date of Patent: Oct. 28, 2008

(54) THIN SEMICONDUCTOR FILM GAS SENSOR DEVICE

(75) Inventors: Giorgio Sberveglieri, Cavriago (IT); Elisabetta Comini, Brescia (IT); Guido Faglia, Gussago (IT); Camilla Baratto, Brescia (IT); Matteo Falasconi, Desenzano Del Garda (IT)

(73) Assignee: Sacmi Cooperativa Meccanici Imola Soc. Coop. a.r.l., Imola (Bologna) (IT)

( * ) Notice: Subject to any disclaimer, the term of this patent is extended or adjusted under 35 U.S.C. 154(b) by 765 days.

(21) Appl. No.: 10/830,133

(22) Filed: Apr. 23, 2004

(65) Prior Publication Data

US 2004/0211667 A1    Oct. 28, 2004

(30) Foreign Application Priority Data

Apr. 24, 2003    (IT)    .......................... TO2003A0318

(51) Int. Cl.
*G01N 7/00* (2006.01)
(52) U.S. Cl. ..................................... 73/31.06
(58) Field of Classification Search ................. 73/31.06
See application file for complete search history.

(56) References Cited

U.S. PATENT DOCUMENTS

| | | | |
|---|---|---|---|
| 3,503,030 A * | 3/1970 | Matsumoto et al. ............ 338/23 |
| 4,169,369 A * | 10/1979 | Chang ........................ 73/31.06 |
| 4,338,281 A | 7/1982 | Treitinger et al. |
| 4,389,373 A | 6/1983 | Linder et al. |
| 4,399,424 A * | 8/1983 | Rigby .......................... 338/34 |
| 4,453,151 A * | 6/1984 | Leary et al. ................... 338/34 |
| 4,457,161 A | 7/1984 | Iwanaga et al. |
| 4,580,439 A * | 4/1986 | Manaka ...................... 73/31.06 |
| 4,673,910 A * | 6/1987 | Uchikawa et al. ............. 338/35 |
| 4,740,387 A * | 4/1988 | Manaka ....................... 427/125 |
| 4,816,800 A * | 3/1989 | Onaga et al. .................. 338/34 |
| 4,885,929 A * | 12/1989 | Kasahara et al. ........... 73/31.06 |
| 4,911,892 A * | 3/1990 | Grace et al. ................... 422/94 |
| 4,938,928 A * | 7/1990 | Koda et al. .................... 422/98 |
| 4,977,658 A * | 12/1990 | Awano et al. .............. 29/25.01 |
| 4,984,446 A * | 1/1991 | Yagawara et al. .......... 73/31.06 |
| 4,991,424 A * | 2/1991 | Lehto ........................ 73/31.06 |
| 5,003,812 A * | 4/1991 | Yagawara et al. .......... 73/31.06 |

(Continued)

FOREIGN PATENT DOCUMENTS

JP            63231254 A    *    9/1988

OTHER PUBLICATIONS

Sberveglieri et al, "Highly Sensitive and Selective $NO_x$ and $NO_2$ Sensor Based on Cd-doped $SnO_2$ Thin Films," Sensors and Actuators B. 4, 1991, pp. 457-461.

(Continued)

*Primary Examiner*—Hezron E. Williams
*Assistant Examiner*—John Fitzgerald
(74) *Attorney, Agent, or Firm*—Squire, Sanders & Dempsey L.L.P.

(57) ABSTRACT

The gas sensor device of the semiconductor film type comprises, on a single face of it, at least one gas sensor, a resistive heating film and pads for electrical contact of the sensors and of the resistive heating film; the heating element, the gas sensor film and the contact pads are made entirely by sputter deposition.

17 Claims, 9 Drawing Sheets

U.S. PATENT DOCUMENTS

| | | | | |
|---|---|---|---|---|
| 5,012,671 | A | * | 5/1991 | Yagawara et al. ........... 73/31.06 |
| 5,019,885 | A | * | 5/1991 | Yagawara et al. ............ 73/23.4 |
| 5,367,283 | A | | 11/1994 | Lauf et al. |
| 5,457,333 | A | * | 10/1995 | Fukui ......................... 257/253 |
| 5,759,367 | A | * | 6/1998 | Matsuura et al. ............ 204/424 |
| 5,783,153 | A | * | 7/1998 | Logothetis et al. ............ 422/83 |
| 5,837,886 | A | * | 11/1998 | Nakahara et al. ........... 73/31.06 |
| 5,918,261 | A | * | 6/1999 | Williams et al. ........... 73/31.06 |
| 6,012,327 | A | * | 1/2000 | Seth et al. .................. 73/31.06 |
| 6,109,095 | A | * | 8/2000 | Addiego .................... 73/31.06 |
| 6,786,076 | B2 | * | 9/2004 | Raisanen ................... 73/31.05 |
| 2003/0230749 | A1 | * | 12/2003 | Isobe et al. .................... 257/59 |
| 2003/0233864 | A1 | * | 12/2003 | Rodier ...................... 73/24.06 |

OTHER PUBLICATIONS

Sberveglieri et al, "A new technique for the preparation of highly sensitive hydrogen sensors based on $SnO_2(Bi_2O_3)$ thin films," Sensors and Actuators B, 5, 1991, pp. 253-255.

Sberveglieri et al, "A new technique for growing porous $SnO_2(Bi_2O_3)$ thin films as bydrogen gas sensors," Journal of Materials Science Letters 10, 1991, pp. 602-604.

Sberveglieri et al, "A novel PVD technique for the preparation of $SnO_2$ thin films as $C_2H_5OH$ Sensors," Sensors and Actuators B, 7, 1992, pp. 721-726.

Sberveglieri et al, "R.G.T.O: A New Technique for Preparing $SnO_2$ Sputtered Thin Film as Gas Sensors." IEEE, vol. 5, 1991, pp. 165-168.

Sberveglieri, "Classical and novel techniques for the preparation of $SnO_2$ thin-film gas sensors", Sensors and Actuators B, 6, 1992, pp. 239-247.

Sberveglieri et al, "Detection of Sub-ppm $H_2S$ concentrations by means of $SnO_2(Pt)$ thin films, grown by the RGTO technique", Sensors and Actuators B, 15-16, 1993, pp. 86-89.

Sberveglieri,"Novel Trends in the development of semiconducting thin films for gas sensing", Books of Abstracts, International Workshop on New Developments in Semiconducting Gas Sensors, Sep. 13-14, 1993.

Sberveglieri et al, "WO3 sputtered thin films for NOx monitoring", Abstract Eurosensors VIII, Sep. 25-28, 1994.

Sberveglieri, "Recent developments in semiconducting thin-film gas sensors", Sensors and Actuators B, 23, 1995, p. 103-109.

Sberveglieri et al, "A Novel Method for the Preparation of Nanosized $TiO_2$ Thin Films" Advanced Materials, 1996, vol. 8, No. 4, pp. 334-337.

Ferroni et al, "Gas-Sensing Applications of W-Ti-O-based nanosized thin films prepared by r.f. reactive sputtering", Sensors and Actuators B, 44, 1997, pp. 499-502.

Faglia et al, "Electrical and structural properties of $RGTO-In_2O_3$ sensors for ozone", Sensors and Actuators B 57, 1997, pp. 188-191.

Comini et al, "Carbon monoxide response of molybdenum oxide thin films deposited by different techniques", Sensors and Actuators B 68, 2000, pp. 168-174.

Comini et al, "Ti-W-O sputtered thin film as n- or p-type gas sensors", Sensors and Actuators B 70, 2000, pp. 108-114.

Comini et al, "Production and characterization of titanium and iron oxide nano-sized thin films", J. Mater. Res., vol. 16, No. 6, Jun. 2001, pp. 1559-1564.

* cited by examiner

— *Prior Art* —
*FIG.1* 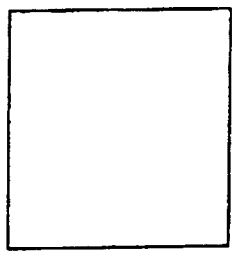 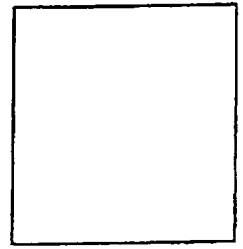 *FIG.4*
*FIG.2* 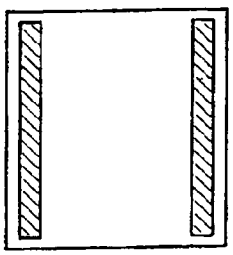 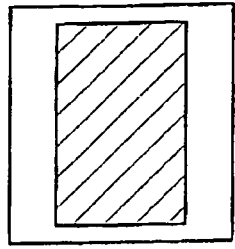 *FIG.5*
*FIG.3* 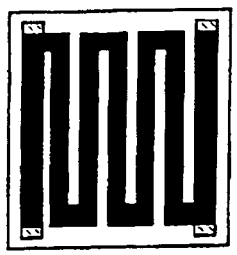 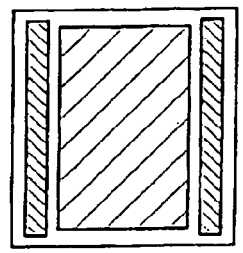 *FIG.6*

EMPTY

FULL

EMPTY

FULL

THIN SEMICONDUCTOR FILM GAS SENSOR DEVICE

BACKGROUND OF THE INVENTION

The present invention relates to a thin semiconductor film gas sensor device of the type comprising an insulating substrate, a thin semiconductor film applied to the substrate and a resistive heating element for heating the substrate and the semiconductor film to a predetermined operating temperature.

Sensor devices of the above mentioned type are very well known to experts in the trade and have been manufactured on a large scale since the nineteen seventies.

Initially, the sensor was made by depositing the film on a tube-shaped ceramic substrate and using as heating element a wire made of a high-melting metal.

According to recent manufacturing methods, improved sensor reproducibility can be obtained using an alumina substrate having, on one face, the heating element made of conductive materials, and on the other, the gas sensor film and the electrical contacts.

A full survey of sensor production methods based on sputter deposition (sputtering) of all the films constituting the sensor is provided by the references listed below, numbered 1-16:

[1] G. Sberveglieri et al., *Sensors and Actuators* B 4 (1991), pages 457-461, Elsevier Sequoia S. A., Lausanne;

[2] G. Sberveglieri et al., *Sensors and Actuators* B 5 (1991), pages 253-255, Elsevier Sequoia S. A., Lausanne;

[3] G. Sberveglieri et al., *Journal of Materials Science Letters* 10 (1991), pages 602-604, Chapman and Hall;

[4] G. Sberveglieri et al., *Sensors and Actuators* B 7 (1992), pages 721-726, Elsevier Sequoia;

[5] G. Sberveglieri, G. Faglia, S. Groppelli, P. Nelli, *Tech. Digest 6th Int. Conf. Solid State Sensors and Actuators*, San Francisco, Calif., USA (1991), pages 165-168;

[6] G. Sberveglieri, *Sensors and Actuators* B 6 (1992), pages 239-247, Elsevier Sequoia S.A.;

[7] G. Sberveglieri et al., *Sensors and Actuators* B 15-16 (1993), pages 86-89, Elsevier Sequoia S.A.;

[8] G. Sberveglieri, *Abstract New Developments in Semiconducting Gas Sensors* Sept. 13-14, 1993, Castro Marina (Italy);

[9] G. Sberveglieri, S. Groppelli, P. Nelli, *Abstract Eurosensors VIII* Sept. 25-28, 1994, Tolouse (France);

[10] G. Sberveglieri, *Sensors and Actuators* B 23 (1995), pages 103-109, Elsevier Science S.A.;

[11] G. Sberveglieri et al., *Advanced Materials* 8 No. 4 (1996), pages 334-337, VCH Verlagsgesellschaft mbH;

[12] M. Ferroni et al., *Sensors and Actuators* B 44 (1997), pages 499-502, Elsevier Science S.A.;

[13] G. Faglia et al., *Sensors and Actuators* B 57 (1999), pages 188-191, Elsevier Science S.A.;

[14] E. Comini et al., *Sensors and Actuators* B 68 (2000), pages 168-174, Elsevier Science S.A.;

[15] E. Comini et al., *Sensors and Actuators* 70 (2000), pages 108-114, Elsevier Science B.V.;

[16] E. Comini et al., *J. Mater. Res.*, 16 No. 6 (2001), pages 1559-1564, Material Research Society.

In most cases, sensor film patterning is obtained using shadow mask technology.

FIGS. 1 to 7, relating to prior art, schematically illustrate the steps in the production of a double-sided sensor.

The overall process comprises two steps for the lower face, that is to say, depositing the pads (rheophores) and depositing the heating element, and three steps for the upper face, comprising the steps of depositing the film, the pads and the interdigitized electrodes.

The prior art method described above has inherent limitations, mainly when the four pins come to be soldered to the substrate and to the microelectronic case which may be, for example, a T08 or similar type of package.

Firstly, when the two wires have to be soldered to the heating element after first soldering the two gas sensor film wires, or vice versa, it is necessary to turn the substrate over. This is quite a difficult operation which slows down the soldering process and may lead to damage to the films making up the sensor.

Secondly, the substrate cannot be soldered directly to the case but must be soldered in two steps:

first soldering the wires to the sensor, and then soldering to the case.

This further slows down the production process.

SUMMARY OF THE INVENTION

One aim of the present invention is to provide an improved gas sensor device that reaches operating temperature quickly and efficiently and that also provides a temperature signal.

According to one aspect of it, the present invention provides a gas sensor device as defined in claim 1.

Another aim of the present invention is to provide a method for the production of a gas sensor device whereby at least one gas sensor element and one resistive heating element are made by successive deposition steps.

According to another aspect of it, the present invention provides a method for making a gas sensor device as defined in claim 8.

The dependent claims describe preferred, advantageous embodiments of the invention.

BRIEF DESCRIPTION OF THE DRAWINGS

The preferred embodiments of the invention will now be described, without restricting the scope of the inventive concept, with reference to the accompanying drawings in which:

FIGS. 1 to 7 schematically illustrate the steps in the production of a double-sided sensor of known type, as discussed above, and, more specifically:

FIG. 1 illustrates the lower face of the sensor as it is initially;

FIG. 2 illustrates the lower face of the gas sensor after deposition of the pads;

FIG. 3 illustrates the lower face of the gas sensor after deposition of the heating element;

FIG. 4 illustrates the upper face of the gas sensor as it is initially;

FIG. 5 illustrates the upper face of the gas sensor after deposition of the film;

FIG. 6 illustrates the upper face of the gas sensor after deposition of the pads;

FIG. 7 illustrates the upper face of the gas sensor after deposition of the interdigitized contacts;

DESCRIPTION OF THE PREFERRED EMBODIMENTS

Figure 11:
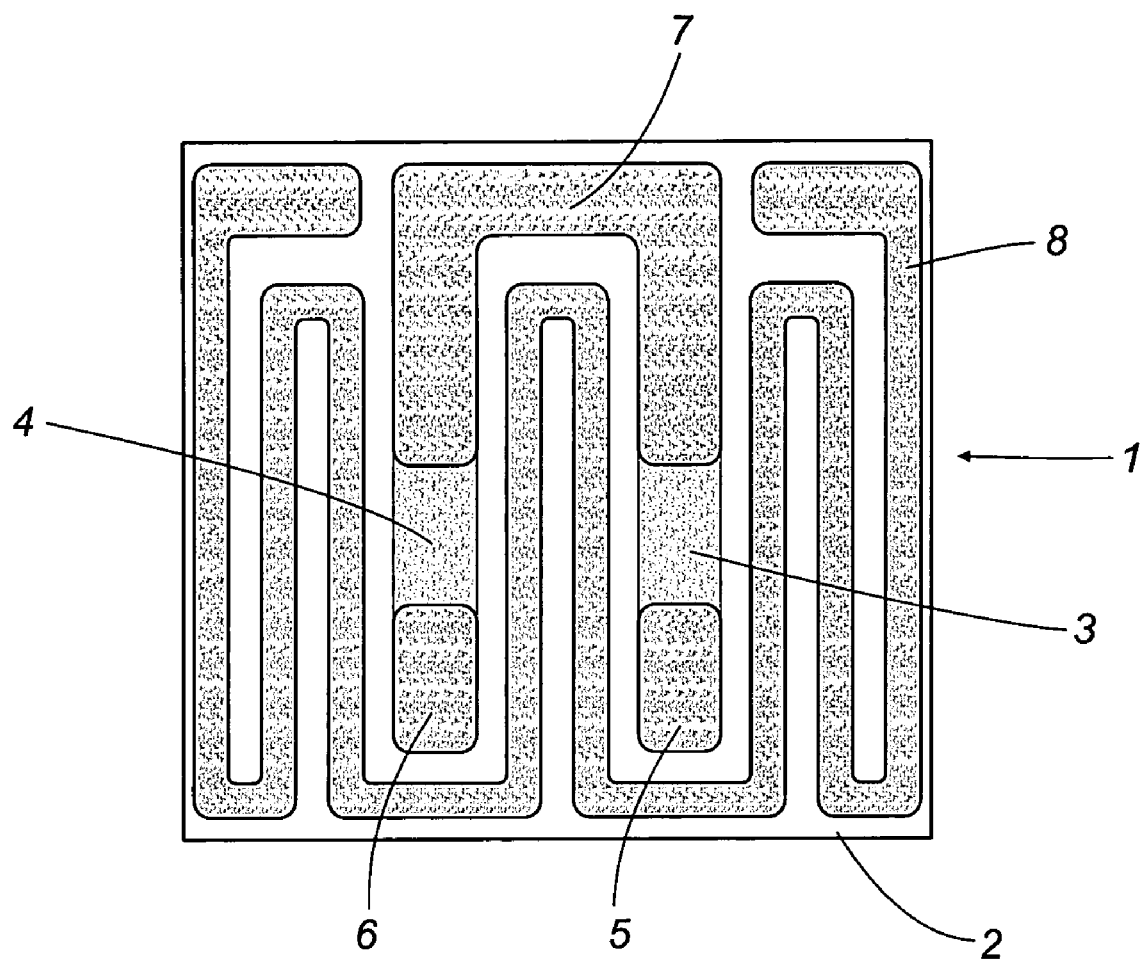
FIG. 11 is an image recorded with an optical microscope of a sensor according to the invention.
Figure 12:
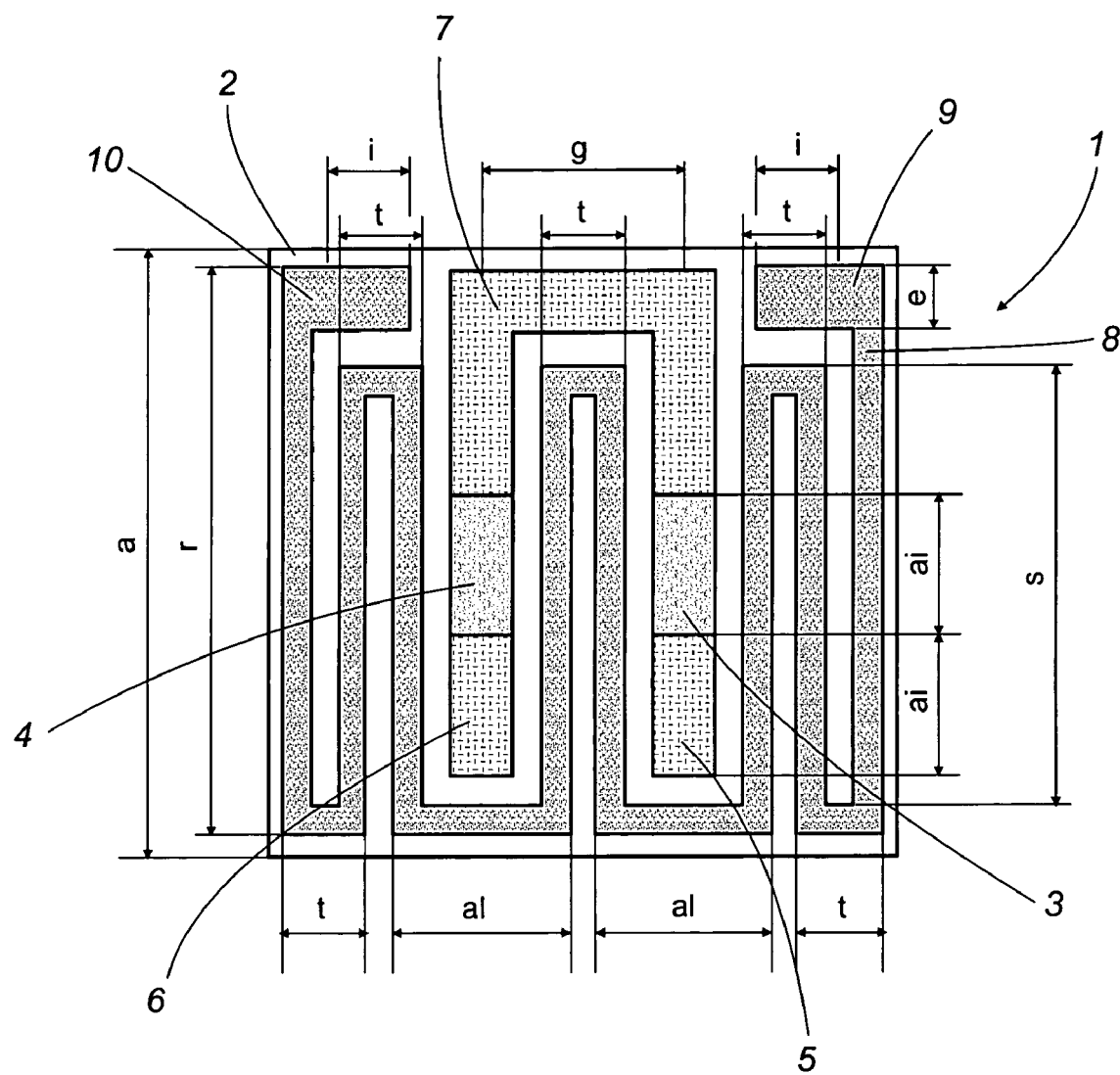
FIG. 12 schematically illustrates the sensor of FIG. 11.

The description that follows is provided purely by way of example and refers to a specific preferred embodiment of the sensor device, as illustrated in FIGS. 11 and 12. The device, denoted in its entirety by the numeral 1, comprises an insulating substrate 2, having on a single face of it gas sensors made from two semiconductor films 3, 4, each in electrical contact with respective conductive pads connected to an instrument for measuring the electrical resistance of the sensors, labeled 5, 6 and 7, and a resistive heating element 8 provided with contact pads 9 and 10 connected to an electric power source.

The substrate 2 is typically made of alumina but the invention also contemplates the use of other types of substrate, such as substrates made of silicon coated with an insulating layer.

The table below shows the dimensions—in millimeters—indicated by letters in the accompanying drawings.

These dimensions are given for information purposes only and are non-restrictive. Thus, for example, the substrate may measure 3 mm×3 mm (dimension "a"), but it might also be smaller, for example 2 mm×2 mm, with a thickness in the order of approximately 250 μm.

| | |
|---|---|
| a = | 3.0 |
| b = | 1.24 |
| c = | 0.88 |
| d = | 0.87 |
| e = | 0.3 |
| f = | 0.66 |
| g = | 1.0 |
| h = | 0.33 |
| i = | 0.4 |
| l = | 0.27 |
| m = | 0.10 |
| n = | 1.82 |
| o = | 0.38 |
| p = | 0.92 |
| q = | 0.76 |
| r = | 2.8 |
| s = | 2.16 |
| t = | 0.42 |
| u = | 0.54 |
| v = | 0.62 |
| z = | 0.60 |
| aa = | 0.05 |
| ab = | 0.14 |
| ac = | 0.12 |
| ad = | 0.2 |
| ae = | 0.82 |
| af = | 0.64 |
| ag = | 0.98 |
| ah = | 1.28 |
| ai = | 0.71 |
| al = | 0.81 |

The substrate 2 can have a surface area of between 1 and 25 $mm^2$, and preferably between 4 and 9 $mm^2$.

Figure 7:
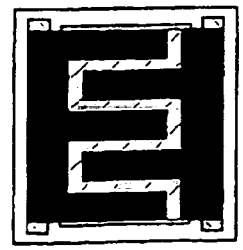
Figure 8:
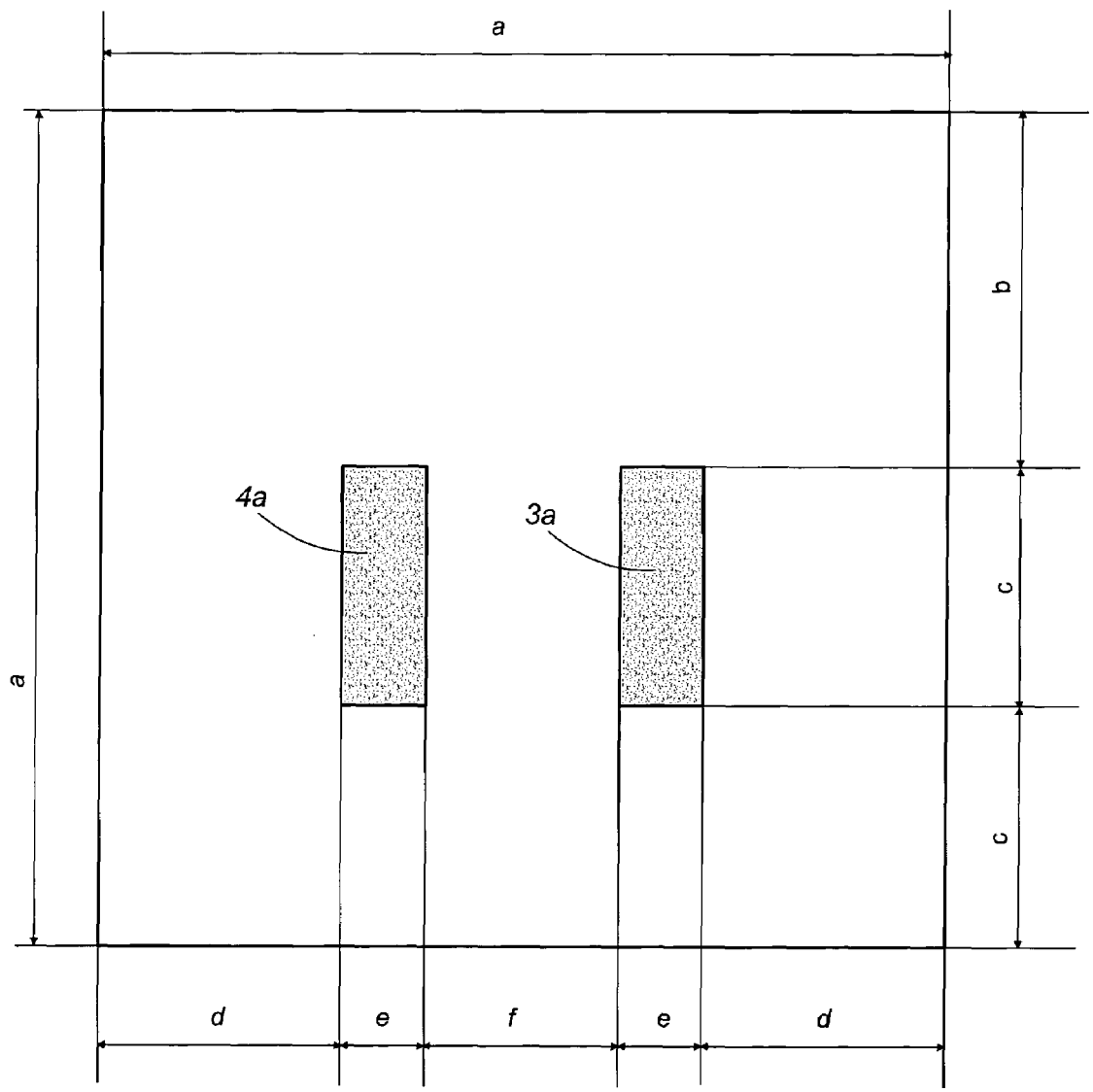
FIG. 8 schematically illustrates a first shadow mask for depositing the sensor film.
Figure 8:
Figure 8:
Figure 9:
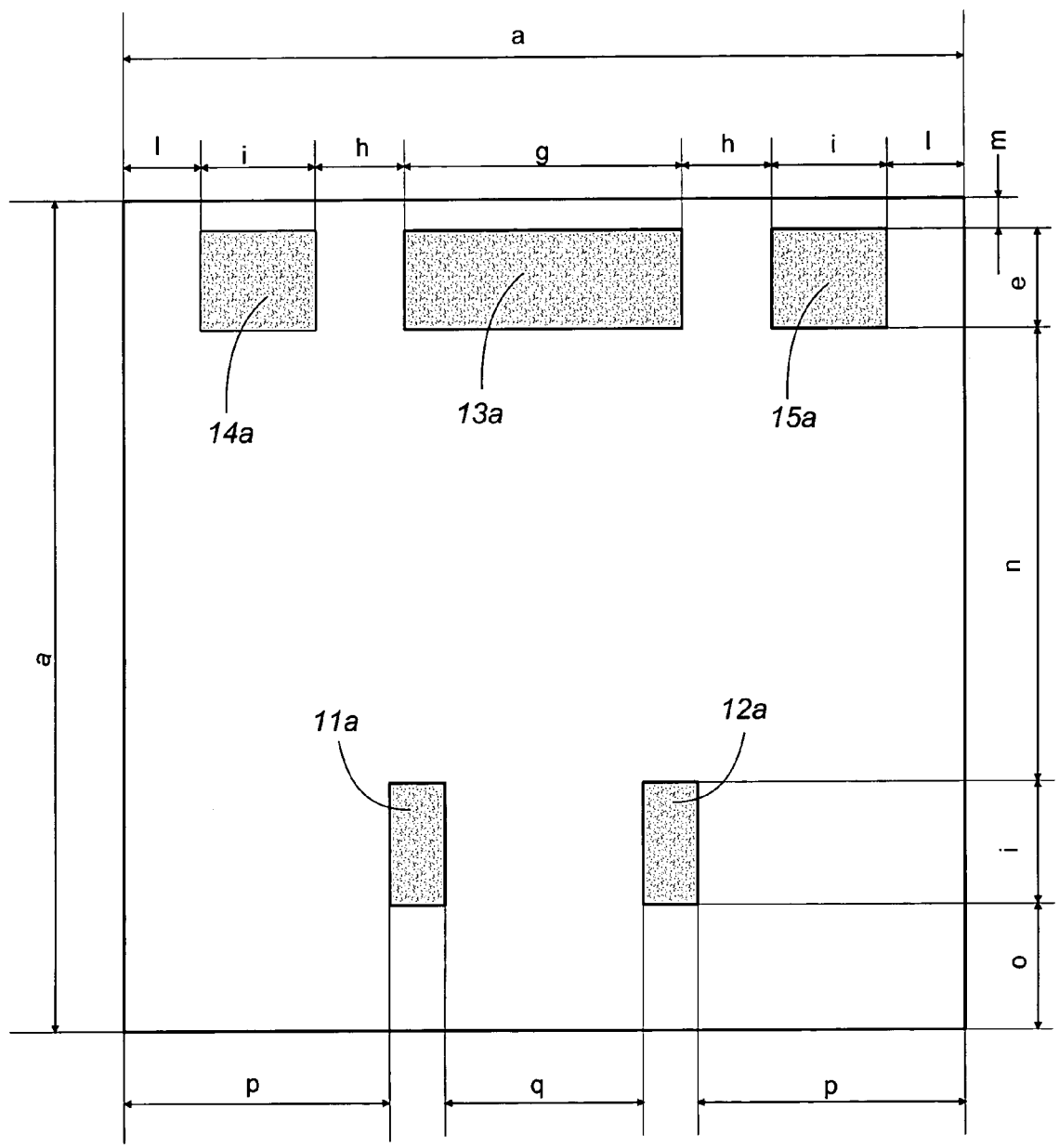
FIGS. 9 and 10 schematically illustrate a second and a third shadow mask used for making the contact pads.
Figure 9:
Figure 9:
Figure 10:
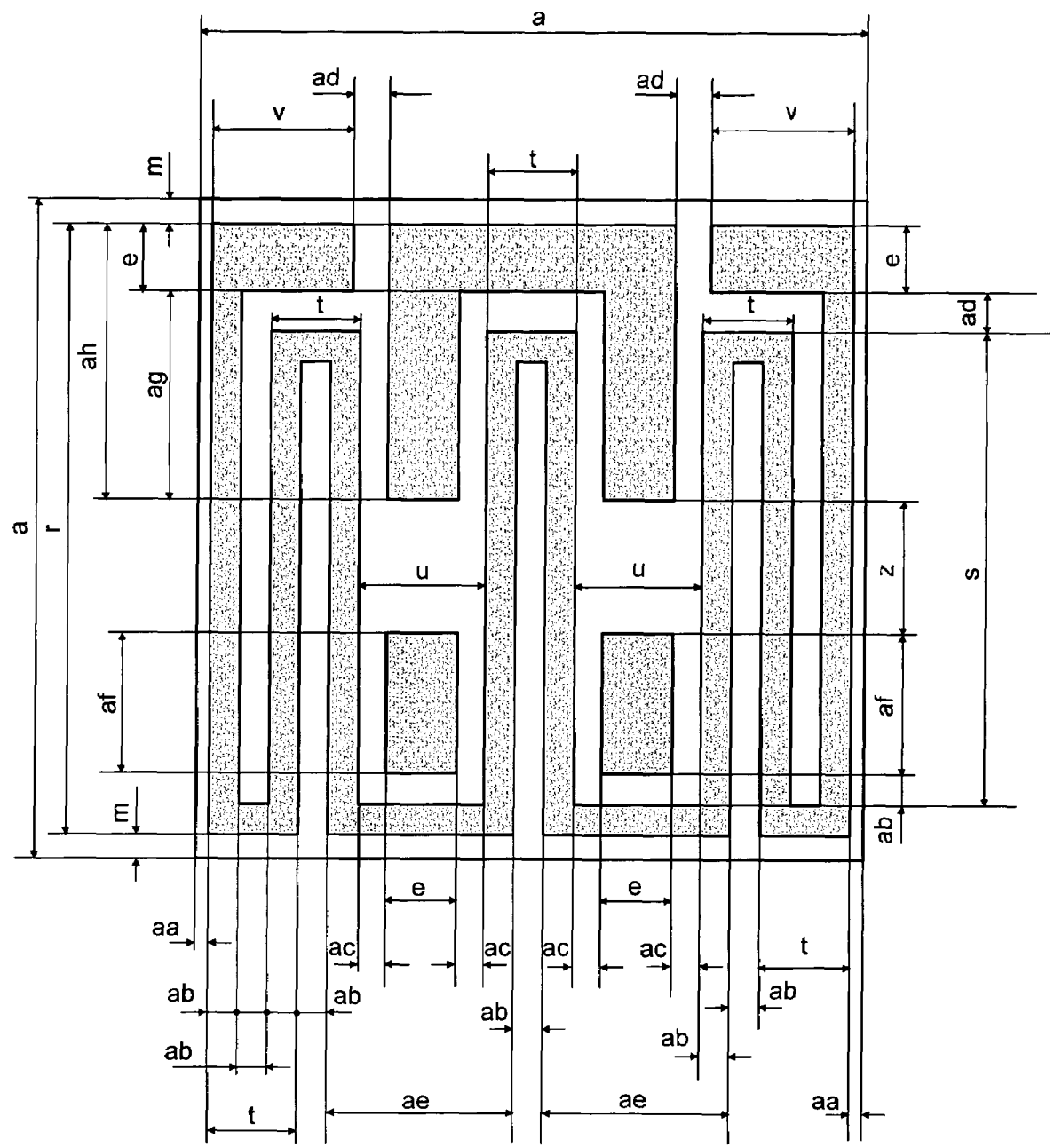

The deposition of the sensor films of the heating element and of the related contact pads is performed by sputtering or cathodic pulverization using shadow masks like the ones illustrated in FIGS. 8, 9 and 10.

The first step is to deposit the sensitive film using a mask (FIG. 8) having only two openings 3a and 4a, positioned preferably in the central portion of the substrate. If two different sensitive films have to be deposited, the mask of FIG. 8 will have a single opening and will be used in two successive deposition processes.

The chemical composition of the semiconductor film is known to experts in the trade and comprises metal oxides such as tin, zinc and iron oxide.

Once the sensitive film has been deposited and, if necessary, oxidized/thermally stabilized, the process continues with the deposition of the contact pads used for soldering the gold wires. The deposition of the contact pads permits gauging of the electrical properties of the sensitive films and makes it possible to power the resistive heating element 8, consisting preferably of noble metal (platinum) with a serpentine pattern, which is designed to reach the operating temperature and which can also be used as a temperature sensor.

The deposition of the contact pads is carried out preferably in two steps. In a first step, titanium/tungsten adhesion layers are deposited on the substrate 2 using a mask like the one illustrated in FIG. 9 which, for this purpose, has two openings 14a and 15a for making the adhesion layers for the contact pads 9 and 10 of the resistive heating element 8 and three openings 11a, 12a and 13a for making the sensitive film contact pads 5, 6 and 7, the opening 13a being for the adhesion layer for the earth contact.

In a second step, the resistive heating element 8 of noble metal (platinum) and a second layer of noble metal (platinum) are deposited over the above mentioned adhesion layers. This step is carried out using a mask like the one illustrated in FIG. 10 which has openings 8a, 9a and 10a used, respectively, for patterning the resistive heating element 8 and the second layer of noble metal (platinum) of the contact pads 9 and 10, and openings 5a, 6a and 7a used for patterning the second layer of platinum for the contact pads 5, 6 and 7 of the two sensitive films.

The thickness of this deposition layer depends on the type of measurements to be carried out, on the required temperature range and on the voltage to be applied to the heating element.

In the currently preferred configuration, the resistive heating element 8 presents a serpentine pattern with a plurality of curves, and the two sensitive semiconductor films 3 and 4 are arranged on the substrate in such a way that they are inside two non-consecutive curves of the serpentine with the opening on the same side.

In this embodiment, the contact pads of the semiconductor films preferably comprise a U-shaped element 7, whose branches—whose ends are respectively in contact with the two semiconductor films 3 and 4—extend into the two non-consecutive curves.

It will be understood that the pattern of the resistive heating element may differ from the one described and illustrated herein, so as to reach the same operating temperature with less electrical power.

Figure 13:
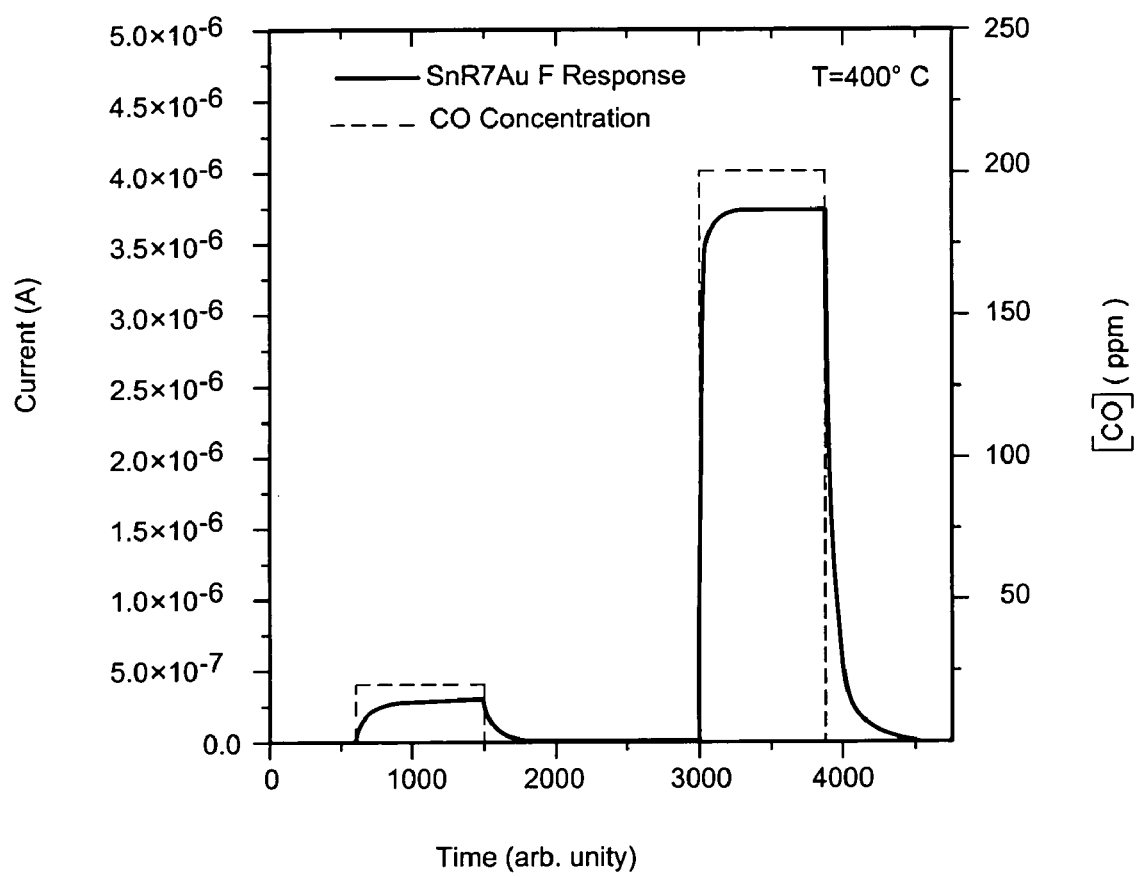
FIGS. 13 and 14 are diagrams respectively illustrating the response to two concentrations of CO (20, 200 ppm) of the first and second $SnO_2$ semiconductor sensor of the device according to the invention.
Figure 14:
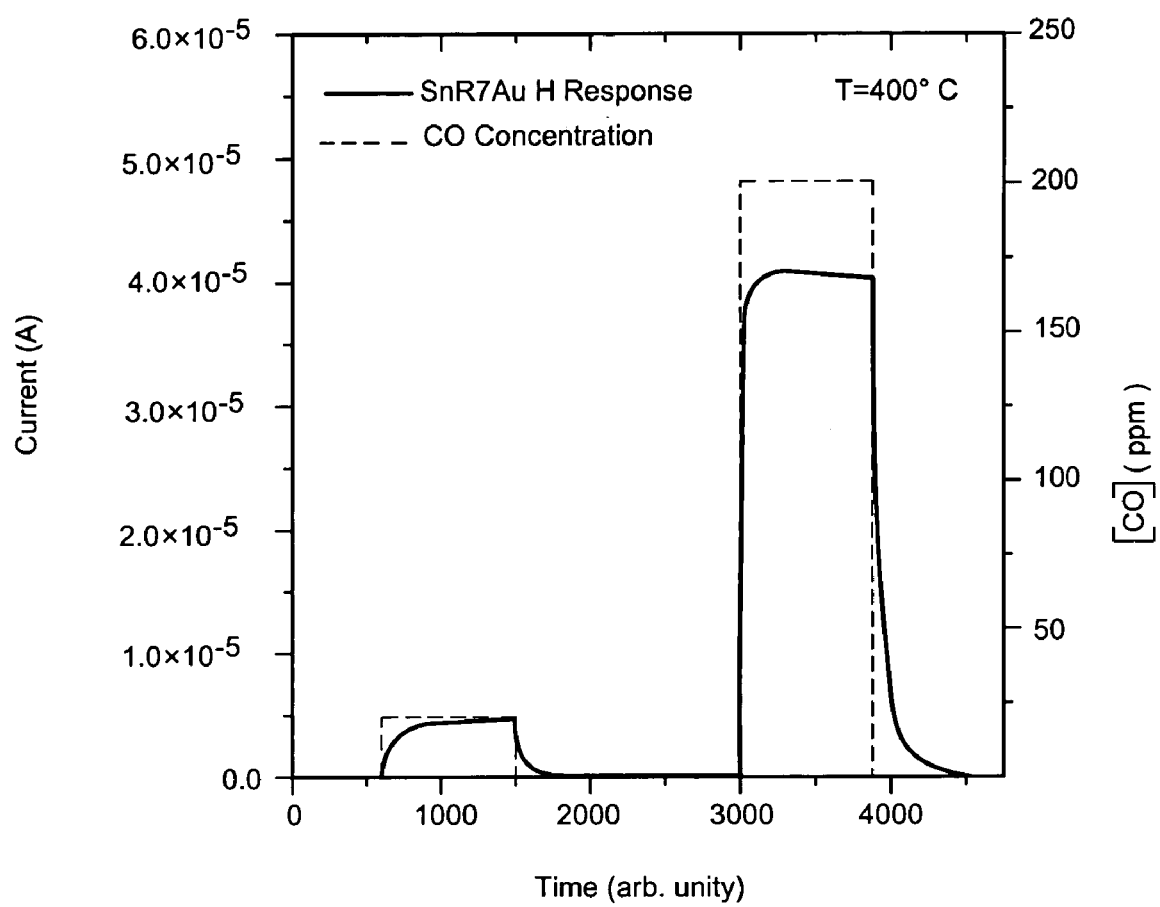
Figure 15:
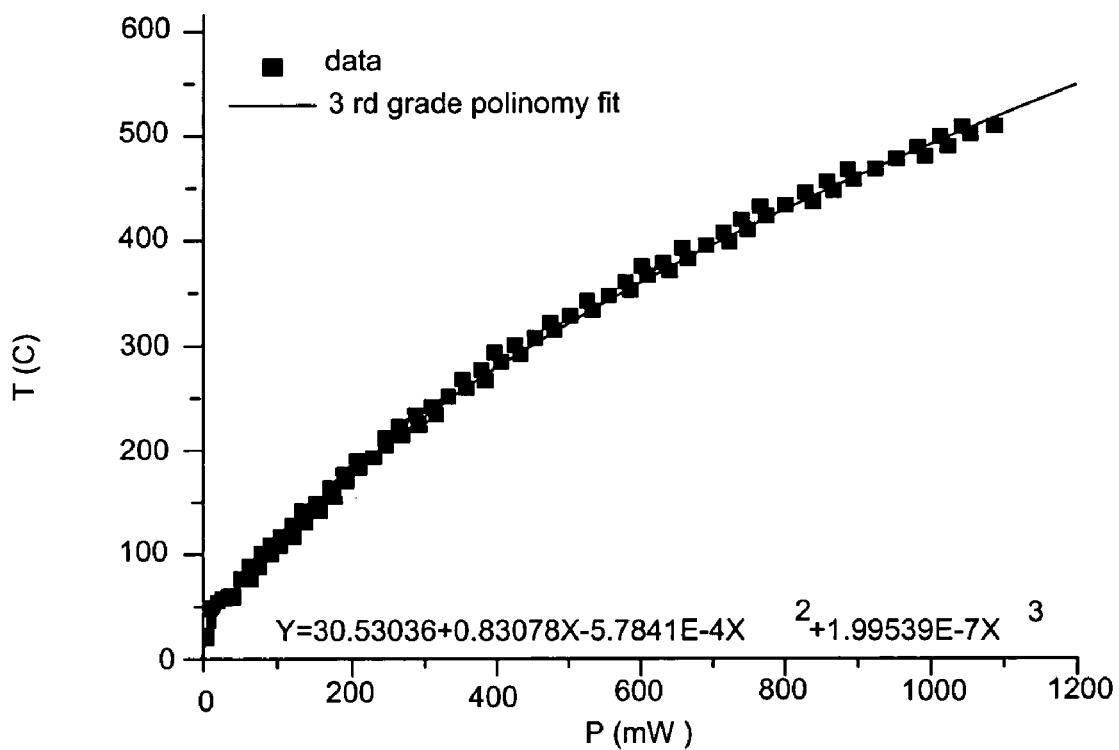
FIG. 15 shows the temperature-power calibration curve for a device according to the invention.

The diagrams of FIGS. 13 and 14 show the results of the electrical characterization performed on the two $SnO_2$ sensor films of the device according to the invention.

The device was tested using carbon monoxide at three different concentrations: 5 (not shown in the diagram), 20 and 200 ppm. The graphs show the variation of electrical current with variations in CO concentration at an operating temperature of 400° C. The response curves for both sensor films in the device are almost identical.

Thanks to the presence of two gas sensors on a single substrate, two different electrical signals are provided (in the case of two different layers) for the same gas mixture to be analyzed. This increases the selectivity of the sensor, since an adequate analysis of the signals can be performed with suitable algorithms.

A further advantage is the possibility of soldering thin wires more quickly and easily and with less risk of damage to them. The sensitive films and the heating filament can be soldered in sequence without turning over the substrate. Also, with a suitable support, the device can be soldered directly to the case, which may be, for example, a T08 package.

Yet another advantage is that the production process, which requires only three steps, is simpler compared to prior art, since the electrical contacts for both the films and the heating element can be made in a single step.

Moreover, the titanium/tungsten adhesion layers for both the resistive heating element and for the two sensitive film contact pads can also be deposited in a single step.

What is claimed is:

1. A gas sensor device comprising:
    an insulating substrate having two faces;
        at least one separate sensor element having respective contact pads, each separate sensor element being made from thin semiconductor film and being applied to a single face of the substrate;
        a resistive heating element for heating to a predetermined temperature the substrate and the semiconductor film applied to it, the heating element being applied to said single face of the substrate and being equipped with respective contact pads for connection to an electrical power source, wherein the resistive element presents a serpentine pattern with a plurality of curves and wherein each semiconductor film is located in a curve of the serpentine.

2. The gas sensor device according to claim 1, wherein the device comprises a plurality of separate sensor elements, preferably from two to four sensors, each separate sensor element being applied to said single face of the substrate.

3. The gas sensor device according to claim 1 or 2, wherein the substrate is made of alumina.

4. The gas sensor device according to claim 1 or 2, wherein the substrate is made of silicon coated with an insulating layer.

5. The gas sensor device according to claim 1 or 2, wherein the substrate has a surface area of between 1 and 25 mm$^2$, preferably between 4 and 9 mm$^2$.

6. The gas sensor device according to claim 1 or 2, wherein the contact pads comprises a first layer made from titanium, deposited on the substrate, and a second superposed layer of platinum.

7. The gas sensor device according to claim 1 or 2, wherein the contact pads comprises a first layer made from tungsten, deposited on the substrate, and a second superposed layer of platinum.

8. A gas sensor device comprising:
    an insulating substrate having two faces;
    at least two separate sensors elements having respective contact pads, each separate sensor element being made from thin semiconductor film in contact with the respective contact pads and being applied to a single face of the substrate;
    a resistive heating element for heating to a predetermined temperature the substrate and the semiconductor film applied to it, the heating element presenting a serpentine pattern with a plurality of curves, being applied to said single face of the substrate and being equipped with respective contact pads for connection to an electrical power source;
    each contact pads for connection of the semiconductor films including a U-shaped element, whose branches, which are in contact with a respective semiconductor film, extend into the curves of the resistive heating element.

9. The gas sensor device according to claim 8, wherein the contact pads comprises a first layer made from titanium, deposited on the substrate, and a second superposed layer of platinum.

10. The gas sensor device according to claim 8, wherein the contact pads comprises a first layer made from tungsten, deposited on the substrate, and a second superposed layer of platinum.

11. The gas sensor device according to claim 8, wherein the semiconductor film is made of tin oxide.

12. The gas sensor device according to claim 8, wherein the semiconductor film is made of zinc oxide.

13. The gas sensor device according to claim 8, wherein the semiconductor film is made of iron oxide.

14. A method for making a sensor device according to claim 1 or 8, comprising the steps of:
    depositing by sputtering at least one separate sensor element made from thin semiconductor film on a single face of the substrate;
    depositing metal adhesion layers on the substrate face to make the contact pads for connection of the sensor elements and of the resistive heating element; and
    depositing over the adhesion layers on the substrate face a conductive film of noble metal according to a pattern that forms the resistive heating element and a second conductive layer of noble metal.

15. The method for making a sensor device according to claim 14, wherein the step of depositing metal adhesion layers makes a layer of titanium for the contact pads for connection of the sensor elements and of the resistive heating element.

16. The method for making a sensor device according to claim 14, wherein the step of depositing metal adhesion layers makes a layer of tungsten for the contact pads for connection of the sensor elements and of the resistive heating element.

17. The method for making a sensor device according to claim 14, wherein the step of depositing by sputtering a separate sensor element is made for a plurality of time, whereby a plurality of separate sensor elements are deposited on a single face of the substrate.

* * * * *

UNITED STATES PATENT AND TRADEMARK OFFICE
CERTIFICATE OF CORRECTION

PATENT NO. : 7,441,440 B2 Page 1 of 1
APPLICATION NO. : 10/830133
DATED : October 28, 2008
INVENTOR(S) : Giorgio Sberveglieri et al.

It is certified that error appears in the above-identified patent and that said Letters Patent is hereby corrected as shown below:

On the Title Page, item (73) the Assignee should read:

SACMI COOPERATIVA MECCANICI IMOLA SOCIETA' COOPERATIVA

Signed and Sealed this

Twenty-first Day of April, 2009

JOHN DOLL
*Acting Director of the United States Patent and Trademark Office*